United States Patent [19]

Tazuma

[11] Patent Number: 4,463,178
[45] Date of Patent: Jul. 31, 1984

[54] METHOD OF PREPARING DIBENZOTHIAZOLYL DISULFIDES

[75] Inventor: James J. Tazuma, Stow, Ohio

[73] Assignee: The Goodyear Tire & Rubber Company, Akron, Ohio

[21] Appl. No.: 453,323

[22] Filed: Dec. 27, 1982

[51] Int. Cl.³ .......................................... C07D 417/12
[52] U.S. Cl. ................................................... 548/158
[58] Field of Search ........................................ 548/158

[56] References Cited

FOREIGN PATENT DOCUMENTS 442954 2/1936 United Kingdom ................ 548/158

Primary Examiner—Richard Raymond
Assistant Examiner—D. B. Springer
Attorney, Agent, or Firm—D. O. Nickey

[57] ABSTRACT

There is disclosed an improved method of preparing dibenzothiazolyl disulfides by oxidizing mercaptobenzothiazole with hydrogen peroxide in the presence of an amine. The invention has particular utility by providing a relatively pollution free method of preparing dibenzothiazolyl disulfides.

9 Claims, No Drawings

METHOD OF PREPARING DIBENZOTHIAZOLYL DISULFIDES

TECHNICAL FIELD

This invention relates to a low pollution process for the manufacture of dibenzothiazolyl disulfide. This process uses dilute amine solutions of 2-mercaptobenzothiazole. The oxidation is carried out at 65° to 80° C. with a hydroperoxide. The product obtained from crude 2-mercaptobenzothiazole is comparable to commercial quality dibenzothiazolyl disulfide.

BACKGROUND ART

Dibenzothiazolyl disulfides are known as accelerators in the vulcanization of diene rubbers. Dibenzothiazolyl disulfides or benzothiazole disulfides were originally developed for the safe processing of rubber compounds cured above 142° C. This thiazole accelerator continues to be used widely in compounds of all types for major commercial applications. Its activity and scorch properties can be controlled over a wide range by using various combinations of other accelerators.

Dibenzothiazolyl disulfide is presently prepared from mercaptobenzothiazole (MBT) which has been steam stripped to remove volatiles and then pelletized. This MBT is dissolved in caustic and converted to the sodium salt (II).

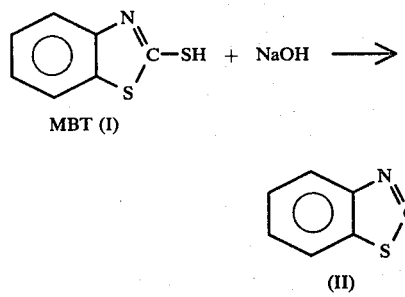

MBT (I)

The salt solution is then extracted with toluene to remove tars. The salt solution is then combined with sodium nitrite. The NaMBT (II) plus NaNO3 solution is then combined with a sulfuric acid solution at 60°–65° C. and converted to dibenzothiazolyl disulfide with by-products of Na2SO4 and NO. NO is known to react with secondary amines such as dimethylamine, to form nitrosamines which are carcinogens. Therefore, there is a need for a process to prepare dibenzothiazolyl disulfide which does not pollute the air and water.

It is known to oxidize the sodium salt of mercaptobenzothiazole in a neutral or alkali medium with halogens or ammonium persulfate. In this system the inorganic by-products resulting from the reaction, such as the inorganic salt produced by neutralizing the mineral acid, must be especially treated or discharged as environmental pollutants. It is, therefore, advantageous to discover a relatively pollution free process for the preparation of dibenzothiazolyl disulfide.

U.S. Pat. No. 4,143,045 by J. Tazuma and A. Bergomi discloses a method for preparing dibenzothiazolyl disulfides by oxidizing mercaptobenzothiazole in a substantially neutral saturated aliphatic alcohol solution with hydrogen peroxide.

U.S. Pat. No. 3,904,638 by S. Sagawa et al discloses a process for the purification of crude 2-mercaptobenzothiazole wherein the crude 2-mercaptobenzothiazole is dispersed into an aromatic hydrocarbon, filtering the resultant dispersion, dissolving the collected particles into an aqueous caustic alkali and filtering the resulting alkaline solution to given an aqueous solution of the alkali salt of 2-mercaptobenzothiazole of high quality.

German Offenlegungsschrift No. 2800462 discloses the preparation of 2,2'-benzothiazolyl disulfide by the oxidation of 2-mercaptobenzothiazole sodium salt with chlorine.

German Offenlegungsschrift No. 2355897 discloses the preparation of bis(2)-benzothiazolyl disulfide from 2-mercaptobenzothiazole by oxidation with air in the presence of FeCl3.

U.S. Pat. No. 2,024,567 disclosed a process of preparing dithiazolyl disulfides which comprises oxidizing a thiazolyl mercaptan with hydrogen peroxide in the presence of an inorganic acid.

U.S. Pat. No. 2,593,761 is concerned with a process for reducing the mercaptan concentration of a sour petroleum distillate which comprises treating said distillate with t-butyl hydroperoxide or cumene hydroperoxide.

The prior art does not suggest or disclose the unique advantages that can be obtained when an amine is used in combination with the peroxide for the oxidation of 2-mercaptobenzothiazole.

DISCLOSURE OF THE INVENTION

There is disclosed a method of preparing dibenzothiazolyl disulfide which comprises oxidizing mercaptobenzothiazole in an aqueous amine solution with a hydroperoxide.

There is disclosed a process for the preparation of dibenzothiazolyl disulfide which comprises oxidizing mercaptobenzothiazole in an aqueous media with a hydroperoxide, the improvement characterized in that; the aqueous media contains an amine selected from the group comprising ammonia, methyl amine, dimethyl amine, trimethyl amine and diethanol amine.

It has been discovered that the oxidation of 2-mercaptobenzothiazole to dibenzothiazolyl disulfide is effectively and economically conducted in an ammonia medium. The peroxide is used as the oxidizing agent in the preparation of the desired product. An equivalent of hydrogen peroxide will take the reaction to completion in approximately 10 minutes. The oxidation process provides dibenzothiazolyl disulfide in acceptable purity from relatively crude starting materials without the attendant pollution problems associated with processes known heretofore.

It should be understood by a skilled artisan that the process of the instant invention is applicable to preparation of other heterocyclic disulfides which are useful as rubber curatives.

In accordance with this invention it has been discovered that dibenzothiazolyl disulfide can be prepared by oxidizing mercaptobenzothiazole in an amine solution with a hydroperoxide selected from hydrogen peroxide and alkyl hydroperoxides.

In the present invention a small amount of an amine, preferably ammonia, is added to a MBT/H2O slurry. Only a portion of the MBT is dissolved.

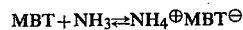

A hydroperoxide, preferably $H_2O_2$, is added which rapidly reacts with $MBT^\ominus$ to yield the dibenzothiazolyl disulfide. The reaction is taken to completion in about 10 minutes at 60° C.–70° C.

The process of the present invention can be specifically described by the following reaction scheme.

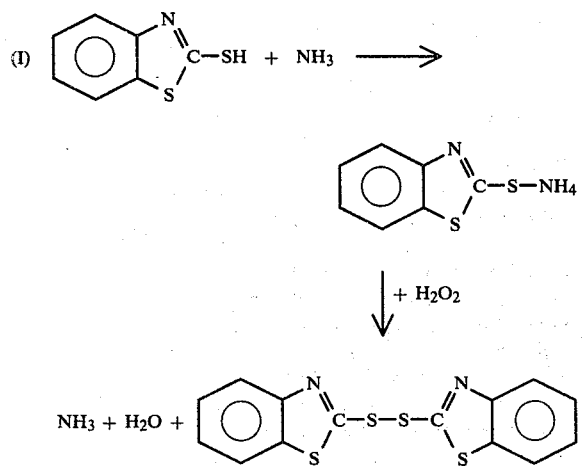

It is an important unexpected result of this invention that the reaction of the peroxide with the mercaptobenzothiazole in the ammonia solution, without the aid of a strong mineral acid, efficiently produces the dibenzothiazolyl disulfide in a relatively high purity form, typically with a yield of about 95 percent. As an example of the unusual purity of the product obtained, without further purification steps the dibenzothiazolyl disulfide typically has a melting point of about 160°–165° C. according to standard capillary tube determinations with a heating rate of about 1° C. per minute.

The important primary advantage of this invention is that the primary by-products are water and regenerated amines instead of the inorganic salt by-products normally produced with the presently accepted oxidizing systems. The amine can be recovered by distillation and thus only water is discharged. Recovery of the amine is enhanced through the adjustment of the filtrate recovered from the process to a pH greater than 8. Another advantage of the present invention is that it can use a lower grade MBT as the starting material.

A mole ratio of hydroperoxide to mercaptobenzothiazole of at least 0.5 is required by the stoichiometry of the reaction. A range of about 0.5 to 0.55 is usually acceptable and is preferred. A smaller ratio can result in insufficient oxidation and a larger ratio can result in overoxidation.

A satisfactory temperature for the relatively fast oxidation reaction is in the range of about 0° C. to about 100° C., preferably about 30° C. to about 80° C. but not appreciably above the boiling point of the reaction mixture.

The reaction can be conducted in bulk or on a continuous basis at atmospheric pressure or above atmospheric pressure. Usually the autogeneous pressure of the mixture is satisfactory. The oxidation is typically fast and efficient without the addition of a strong mineral acid with essentially the only by-product being water. The dibenzothiazolyl disulfide is then simply recovered as a high purity solid product by conventional means such as filtration.

Various hydroperoxides can be used in the mercaptobenzothiazole oxidation step. Representative of the various hydroperoxides are hydrogen peroxide and alkyl hydroperoxides. The alkyl radical of the hydroperoxides are saturated aliphatic radicals having 3 to 6 carbon atoms such as n-propyl, isopropyl, n-butyl, isobutyl, t-butyl, n-penyl, isopentyl, t-pentyl, n-hexyl, isohexyl and t-hexyl radicals. Hydrogen peroxide is preferred.

In general, any amine that is water soluble can be used in this invention. Representative of the amines that are useful in the process of the present invention are ammonia, methyl amine, dimethyl amine, ethyl amine, diethyl amine, ethanol amine, diethanol amine, propanol amine and dipropanol amine. Preferred amines are ammonia, methyl amine, dimethyl amine, trimethyl amine and diethanol amine. The most preferred amine is ammonia.

The amine which is added to the $MBT/H_2O$ slurry in the process of the present invention may be anhydrous or aqueous solutions of the amine.

The concentration of the amine being added to the $MBT/H_2O$ slurry is preferably saturated or highly concentrated solutions thereof. It has been found that concentrations of 0.1 Normal to saturated solutions are appropriate; however, the more concentrated solutions are preferred. In fact, the addition of anhydrous ammonia or other anhydrous amines is advantageous since lower concentrations only result in the unnecessary addition of liquid material to the reaction mixture which eventually has to be dealt with.

To one skilled in chemistry it is readily apparent that anhydrous amines, such as ammonia, will, when placed in an aqueous media, form the hydrates thereof, i.e., aqueous ammonia as well as ammonia hydroxide. The process of the present invention contemplates these hydrates and has found the use of ammonia dissolved in water to be especially useful.

The amount of amine added to the $MBT/H_2O$ slurry can range from 5–300 mole percent based on moles of MBT present in the slurry. A more preferred range is 10–100 mole % while 10–20 mole percent is most preferred. High amounts of amine, i.e. over 50 mole %, do not provide any advantage, increases the cost of distillation to recover the amine, and may cause purity problems in the final product.

The amount of water used to prepare the $MBT/H_2O$ slurry can range from 95 to 60% by weight of the slurry. A preferred range is 90 to 80% $H_2O$ by weight.

The combination of MBT, $H_2O$ and amine slurry useful in the present invention can range from 5 to 30% MBT by weight, with 10–25% MBT more preferred, the most preferred range is 15–22% MBT by weight.

BEST MODE FOR CARRYING OUT THE INVENTION

The practice of this invention is illustrated by reference to the following examples which are intended to be representative rather than restrictive of the scope of this invention. Unless otherwise indicated all parts and percentages are by weight.

The experiments were carried out in a 3-neck flask fitted with a condenser, stirrer, dropping funnel, thermometer and heating mantle. The flask was charged with 2-mercaptobenzothiazole, $NH_4OH$, and water. The mixture was heated to specified temperature and hydrogen peroxide solution was added dropwise. The reaction temperature was allowed to rise due to the heat of reaction. After 5 to 10 minutes of further stirring, the mixture was cooled to approximately 35° C. and filtered. The product was washed with water and dried at 70° C. in an air oven.

Ammonia solution is used as the medium for the oxidation. The ammonia reacts with the 2-mercaptobenzothiazole and yields the ammonium salt which is slightly soluble. This salt is directly converted to the desired product by the hydroperoxide. The slight solubility of the ammonium salt is, however, sufficient for effective conversion provided the hydroperoxide addition takes about 5 to 10 minutes. The minimum mole percentage of ammonia required is near 10 (1 mole $NH_3$/mole MBT) although most of the investigations are carried out at 20 percent.

Different lots of crude 2-mercaptobenzothiazole were utilized. Crude 2-MBT means the product obtained from the reaction of starting materials without purification. The purity of the crude MBT by silver nitrate analysis is 90 percent by weight approximately. The information set out in Table I used the optimum conditions of 19% 2-mercaptobenzothiazole, reaction temperature of 65°–80° C. with an addition time of hydroperoxide of 10 to 15 minutes. Also reported in Table I is settling volume (SV) The main variation seen in Table I is the settling volume which ranged between and 18 and 24 cc.

TABLE I

Conditions: 19% 2-mercaptobenzothiazole (MBT) by weight in $NH_3$ slurry
20 mole % $NH_3$/MBT
9.3% Toluene by weight on total MBT plus toluene
10% excess $H_2O_2$

| Run No. | Rxn T °C./add time (min) | Yield | MP °C. | 5 min. SV (cc) | % Unreacted in Final Product |
|---|---|---|---|---|---|
| 1 | 64–80/15 | 93.5 | 162–166 | 20. | 0.73 |
| 2 | 67–72/17 | 92.7 | 158–166 | 18 | 0.49 |
| 3 | 65–72/17 | 93.5 | 158–166 | 21 | 0.73 |
| 4 | (10 mole % $NH_3$) 68–82/11 | 91.9 | 158–166 | 24 | 0.50 |
| 5 | 64–70/20 | 93.0 | 158–165 | 23 | 0.42 |
| 6 | 61–71/12 | 93.4 | 159–165 | 23.5 | 0.69 |
| 7 | 60–71/11 | 93.4 | 160–165 | 21 | 0.40 |
| 8 | 61–71/12 | 92.5 | 160–165 | 20 | 0.38 |

Settling volume is a measure of the density of the dibenzothiazolyl disulfide formed. A high density (lower S.V.) crystalline product is desired since it fractures easily and is therefore readily dispersed into the rubber during milling operations.

An accepted S.V. in the industry is 20. S.V. is determined by taking 5 grams of final product and suspending it in a 100 cc total volume of methanol. The suspended sample is allowed to stand for 5 minutes and the volume of settled dibenzothiazolyl disulfide is measured.

Toluene was used as an additive to control SV. As can be seen from Table II about 9.3% toluene is needed in a batch process to obtain an settling volume of 18 to 24 cc. Further increase in toluene decreases SV, however, larger amounts (17%) lowers product quality.

Table III sets out the effect of the purity of the MBT starting material. Analysis of crude MBT by titiation indicates that the MBT from the reactor and pelletizer unit is ≈90% by weight. One part of crude MBT is washed with 2 parts of toluene at 70° C. to effect purification. Analysis of the washed MBT indicates approximately 94% purity.

TABLE II

Conditions: 19% 2-mercaptobenzothiazole (MBT) by weight in $NH_3$ slurry
20 mole % $NH_3$/MBT
9.3% Toluene by weight on total MBT plus toluene
10% Excess $H_2O_2$

| Run No. | % Toluene (MBT) | Rxn T °C./add time (min) | Yield | MP °C. | 5 (min) SV (cc) | % Unreacted MBT in Final Prod. |
|---|---|---|---|---|---|---|
| 9 | 0 | 65–78/10 | 92.8 | 158–163.5 | 39 | 1.29 |
| 10 | 4.9 | 63–76/10 | 93.1 | 160–166 | 27 | 0.86 |
| 11 | 9.3 | 64–72/17 | 92.7 | 158–166 | 18 | 0.49 |
| 12 | 9.3 | 61–75/12 | 93.4 | 159–165 | 23.5 | 0.69 |
| 13 | 11 | 64–75/13 | 93.0 | 159–165 | 17 | 0.35 |
| 14 | 17 | 59–60/13 | 84.4 | 157–162 | 14 | 7.0 |

TABLE III

Effect of MBT Concentration

Conditions: 10 mole % $NH_3$
9.3% Toluene (start) + 9.3% Toluene (end)
Crude MBT Washed With Toluene To Remove Tars

| Run No. | % MBT | Rxn T °C./Add time (min) | $H_2O_2$ Excess | % Yield | MP °C. | 5 min SV (cc) | % MBT |
|---|---|---|---|---|---|---|---|
| 15 | 11.8 | 74–80/12 | 40% | 93.5 | 158–163 | 24 | 4.9 |
| 16 | 16.5 | 60–78/12 | 10% | 92.3 | 155–162 | 24 | 7.8 |
| 17 | 20.5 | 60–78/10 | 10% | 93.5 | 158–165 | 23 | 2.4 |

Compare with data from Table I for Unpurified MBT

EXAMPLE OF PROCESS USING HIGH PURITY MBT (99%)

A 500 cc three-neck flask was charged with 12 g purified MBT, 0.425 g concentrated $NH_3$ (28%) and 100 cc of distilled water. The mixture was warmed to 60° C. and 1.35 g of hydrogen peroxide diluted to 45 cc with distilled water was added to the reaction flask with stirring over 16 minutes. After 15 minutes of reaction the product was filtered and dried. There was obtained 11 g of product with a melting point of 171°–175° C.

EXAMPLE OF CONTINUOUS PROCESS

To a 9.5 liter stirred reactor jacketed at 82° C. was charged two streams; stream A was a 8.6% aqueous slurry of MBT containing 20 mole percent ammonia based on moles of MBT which was preheated to 48° C. and; stream B was a 10% by weight aqueous solution of $H_2O_2$. The flow rates were 475 c.c./min. of stream A and 48.9 c.c./min. of stream B. The average residence time in the reactor was 18.1 min. and the reaction mixture was held at 75° C.±2° C. After a period of operation a sample was withdrawn, separated and analyzed to have a melting point of 160°–165° C. with a S.V. of 20 and 1.5% unreacted MBT.

The process of the present invention also contemplates a process wherein a heel or seed is utilized to control S.V.

EXAMPLE OF HEEL EFFECT ON SV

To a 500 c.c. three neck flask was charged 31.5 g of crude MBT, 10.5 g of benzothiazolyl disulfide (160°–165° C. melting point with an SV of 19.5 cc) and 175 cc of 0.285N. ammonia solution. This mixture was then heated to 65° C. and 80 cc of 4.5% by weight $H_2O_2$ (20 mole % based on mole of MBT) was added over approximately 9 minutes. The reaction mixture reached a temperature of 76° C. The product was isolated for a yield of 93.9% with 1.15% of the MBT unreacted. The S.V. was 31 cc. The same procedure was used but without the heel to obtain an S.V. of 39 cc.

The advantages of the present invention are:
1. No salt produced in the process from acid-base reactions.
    a. A small amount of acidic material is formed.
    b. This would result in a lower cost of product since caustic (NaOH) and sulfuric acid are eliminated.
2. No gaseous effluent, since water is only product of oxidation. This process eliminates NO discharge.
3. Use of lower grade of MBT.
    a. Eliminates prior art toluene extraction step.
    b. Since tars are partly carried through the process, a higher yield of finished product is obtained based on crude product from autoclave in the manufacture of MBT. The yield will be higher with respect to the starting materials for MBT.

It may be possible in a continuous process to eliminate the use of toluene to control the density of the product. If an S.V. of 30 is acceptable, it would be possible to produce this material without aid of toluene in a batch reaction.

While certain representative embodiments and details have been shown for the purpose of illustrating the invention it will be apparent to those skilled in this art that various changes and modifications may be made without departing from the scope of the invention.

What is claimed:

1. In a process for the preparation of dibenzothiazolyl disulfide which comprises the steps of oxidizing mercaptobenzothiazole in an aqueous media with a hydroperoxide selected from the group consisting of hydrogen peroxide and alkyl hydroperoxides of 3 to 6 carbon atoms, wherein the mol ratio of hydroperoxide to mercaptobenzothiazole is from 0.5 to 0.55, the improvement characterized in that; the aqueous media has dissolved therein ammonia or an amine selected from the group consisting of methyl amine, dimethyl amine, trimethyl amine and diethanol amine wherein the concentration of the ammonia or amine can range from 10 to 100 mol percent based on mols of mercaptobenzothiazole.

2. A process according to claim 1 wherein the hydroperoxide is hydrogen peroxide, the aqueous media has dissolved therein ammonia at a concentration of from 10 to 20 mol percent based on mols of mercaptobenzothiazole.

3. A process according to claim 1 wherein the oxidation takes place at a temperature from 0° to 100° C.

4. A process according to claim 1 wherein the concentration of the mercaptobenzothiazole in the amine water slurry can range from 10–25% by weight.

5. A process for the production of dibenzothiazolyl disulfide which comprises the addition of 0.5 to 0.55 moles of hydrogen peroxide per mole of mercaptobenzothiazolyl present in an aqueous slurry containing at least 10 mole percent ammonia based on moles of mercaptobenzothiazole in the aqueous slurry that is at least 5 percent by weight mercaptobenzothiazole.

6. A process according to claim 5 wherein the mole ratio of hydrogen peroxide to mercaptobenzothiazole is from 0.5 to 0.52.

7. A process according to claim 5 wherein the oxidation takes place at a temperature from 0° to 100° C.

8. A process according to claim 5 wherein the concentration of the ammonia in the mercaptobenzothiazole water slurry can range from 15 to 75 mole percent based on moles of mercaptobenzothiazole.

9. A process according to claim 5 wherein the concentration of the mercaptobenzothiazole in the amine water slurry can range from 10–25% by weight.

* * * * *